(12) United States Patent
Vennerstrom et al.

(10) Patent No.: US 10,531,680 B2
(45) Date of Patent: *Jan. 14, 2020

(54) CREATINE ESTER PRONUTRIENT COMPOUNDS AND FORMULATIONS

(71) Applicant: BOARD OF REGENTS OF THE UNIVERSITY OF NEBRASKA, Lincoln, NE (US)

(72) Inventors: Jonathan L. Vennerstrom, Omaha, NE (US); Donald W. Miller, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 18 days.

This patent is subject to a terminal disclaimer.

(21) Appl. No.: 15/477,160

(22) Filed: Apr. 3, 2017

(65) Prior Publication Data

US 2017/0202241 A1 Jul. 20, 2017

Related U.S. Application Data (63) Continuation of application No. 13/069,697, filed on Mar. 23, 2011, now abandoned, which is a continuation of application No. 11/743,394, filed on May 2, 2007, now abandoned, which is a continuation of application No. 10/363,761, filed as application No. PCT/US01/28788 on Sep. 14, 2001, now abandoned.

(60) Provisional application No. 60/232,969, filed on Sep. 14, 2000.

(51) Int. Cl.
| | |
|---|---|
| A23K 20/142 | (2016.01) |
| A61K 31/198 | (2006.01) |
| A61K 31/221 | (2006.01) |
| A61K 31/66 | (2006.01) |
| A23L 33/10 | (2016.01) |

(52) U.S. Cl.
CPC ............ *A23K 20/142* (2016.05); *A23L 33/10* (2016.08); *A61K 31/198* (2013.01); *A61K 31/221* (2013.01); *A61K 31/66* (2013.01)

(58) Field of Classification Search
CPC .................................................. A23K 20/142
See application file for complete search history.

(56) References Cited

U.S. PATENT DOCUMENTS

| | | | |
|---|---|---|---|
| 3,088,871 A | 5/1963 | Pfeiffer | |
| 5,576,316 A | 11/1996 | Cohn | |
| 5,767,159 A | 6/1998 | Hultman et al. | |
| 5,773,473 A | 6/1998 | Green et al. | |
| 5,866,537 A | 2/1999 | Bianchi | |
| 5,886,040 A | 3/1999 | Fang et al. | |
| 5,994,581 A | 11/1999 | Fang | |
| 6,093,746 A | 7/2000 | Uchida et al. | |
| 6,093,848 A | 7/2000 | Greindl et al. | |
| 6,117,872 A | 9/2000 | Maxwell et al. | |
| 6,136,339 A | 10/2000 | Gardiner | |
| 6,242,490 B1 | 6/2001 | Anelli et al. | |
| 6,242,491 B1 | 6/2001 | Kaddurah-Daouk | |
| 6,413,552 B1 | 7/2002 | Stoll | |
| 6,503,951 B2 | 1/2003 | Pischel et al. | |
| 6,897,334 B2 | 5/2005 | Vennerstrom | |
| 2002/0049253 A1 | 4/2002 | Kaddurah-Daouk | |
| 2003/0212136 A1 | 3/2003 | Vennerstrom et al. | |
| 2003/0212130 A1 | 11/2003 | Miller et al. | |
| 2004/0242691 A1 | 12/2004 | Miller et al. | |
| 2008/0063689 A1 | 3/2008 | Farber | |
| 2008/0103202 A1 | 5/2008 | Ferguson et al. | |
| 2008/0124439 A1 | 5/2008 | Nuralam | |
| 2011/0224174 A1 | 9/2011 | Miller et al. | |

FOREIGN PATENT DOCUMENTS

| | | |
|---|---|---|
| DE | 19929995 | 1/2001 |
| DE | 100 65 478 | 8/2002 |
| GB | 1185882 | 3/1970 |
| GB | 2333706 | 8/1999 |
| JP | 7-509230 | 10/1995 |
| JP | 11-505540 | 5/1999 |
| JP | 8-224073 | 9/1999 |
| JP | 2001-517085 | 10/2001 |
| JP | 2002-510604 | 4/2002 |
| JP | 2002-530330 | 9/2002 |
| WO | 9633707 | 10/1996 |
| WO | 9828263 | 7/1998 |
| WO | 98/43499 | 10/1998 |
| WO | 9951097 | 10/1999 |
| WO | 0010408 | 3/2000 |
| WO | 00/30634 | 6/2000 |
| WO | 0103325 | 1/2001 |
| WO | 0154676 | 8/2001 |
| WO | 0202075 | 1/2002 |

(Continued)

OTHER PUBLICATIONS

Berge et al. ("Pharmaceutical salts" Journal of Pharmaceutical Sciences, 1977, 66, 1, 1-19).*

P. Klivenyi et al., "Neuroprotective effects of creatine in a transgenic animal model of amyotrophic lateral sclerosis", Nature Medicine, 5(3): 347-350 (1999).

R. Matthews et al., "Creatine and Cyclocreatine Attenuate MPTP Neurotoxicity", Experimental Neurology, 157: 142-149 (1999).

B. Willer et al., "Effects of creatine supplementation on muscle weakness in patients with rheumatoid arthritis", Rheumatology, 39: 293-298 (2000).

(Continued)

*Primary Examiner* — Yong S. Chong (74) *Attorney, Agent, or Firm* — Bradley Arant Boult Cummings LLP (57) ABSTRACT

The present invention describes a method for providing creatine to an animal, which includes receiving a creatine ester by the animal. The creatine ester is suitable for being modified by the animal to form creatine.

18 Claims, 9 Drawing Sheets

(56) References Cited

FOREIGN PATENT DOCUMENTS

| WO | 02052957 | 7/2002 |
|---|---|---|
| WO | 02058488 | 8/2002 |
| WO | 2004071406 | 8/2004 |
| WO | 2008151249 | 12/2008 |

OTHER PUBLICATIONS

C. Malcon et al., "Neuroprotective effects of creatine administration against NMDA and malonate toxicity", Brain Research, 860: 195-198 (2000).

J. Mold et al., "Creatine Ethyl Ether", J. Amer. Chem. Soc., 77: 178-180 (1955).

A. Gordon et al., "Creatine supplementation in chronic heart failure increases skeletal muscle creatine phosphate and muscle performance", Cardiovascular Research, 30: 415-418 (1995).

A. Dox et al., "Esterification of Creatine", J. Biological Chemistry, LIV(4): 671-673 (1922).

S. Felber et al., "Oral creatine supplementation in Duchenne muscular dystrophy: a clinical and 31P magnetic resonance spectroscopy study", Neurol. Res., 22(2): 145-150 (2000) [Abstract only].

Miyazaki, Shozo, et al., "Solubility Characteristics of Weak Bases and Their Hydrochloride Salts in Hydrochloric Acid Solutions", Chem. Pharm. Bull., Jan. 29, 1979, pp. 1441-1447.

Miyazaki, Shozo, et al., "Precaution on Use of Hydrochloride Salts in Pharmaceutical Formulation", Journal of Pharmaceutical Sciences, vol. 70, No. 6, Jun., 1981, pp. 594-596.

\* cited by examiner

R = Et, Benzyl, and the like

X = Stearate, Palmitate, Oleate, Lauryl Sulfate, Chloride, Acetate, Succinate, Mesylate, Sulfate, Citrate, and the like

R = Ethyl, Benzyl, and the like

CREATINE ESTER PRONUTRIENT COMPOUNDS AND FORMULATIONS

CROSS-REFERENCE TO RELATED APPLICATIONS

The present application is a continuation of U.S. patent application Ser. No. 13/069,697, filed Mar. 23, 2011 (now abandoned), which is a continuation of U.S. patent application Ser. No. 11/743,394, filed May 2, 2007 (now abandoned), which is a continuation of U.S. patent application Ser. No. 10/363,761, filed Mar. 5, 2003 (now abandoned), which is a § 371 of International Application No. PCT/US01/28788 filed in the United States of America on Sep. 14, 2001, which claims the benefit of U.S. Provisional Application 60/232,969 filed Sep. 14, 2000. The entire disclosure of each of the aforesaid applications is incorporated by reference in the present application.

FIELD OF THE INVENTION

The present invention generally relates to the field of creatine, and particularly to creatine ester pronutrient compounds and formulations.

BACKGROUND OF THE INVENTION

Creatine is an endogenous nutrient produced naturally by the liver in most vertebrates. The uses of creatine are many, including use as a supplement to increase muscle mass and enhance muscle performance as well as in emerging applications in the treatment of neuromuscular disorders.

Typically, creatine is taken up into muscle cells by specific receptors and converted to phosphocreatine by creatine kinase. Muscle cells, including skeletal muscle and the heart muscle, function by utilizing cellular energy released from the conversion of adenosine triphosphate (ATP) to adenosine diphosphate (ADP). The amount of phosphocreatine in the muscle cell determines the amount of time it will take for the muscle to recover from activity and regenerate adenosine triphosphate (ATP). Phosphocreatine is a rapidly accessible source of phosphate required for regeneration of adenosine triphosphate (ATP) and sustained use of the muscle.

For example, energy used to expand and contract muscles is supplied from adenosine triphosphate (ATP). Adenosine triphosphate (ATP) is metabolized in the muscle by cleaving a phosphate radical to release energy needed to contract the muscle. Adenosine diphosphate (ADP) is formed as a byproduct of this metabolism. The most common sources of adenosine triphosphate (ATP) are from glycogen and creatine phosphate. Creatine phosphate is favored as a ready source of phosphate because it is able to resynthesize adenosine triphosphate (ATP) at a greater rate than is typically achieved utilizing glycogen. Therefore, increasing the amount of creatine in the muscle increases the muscle stores of phosphocreatine and has been proven to increase muscle performance and increase muscle mass.

However, creatine itself is poorly soluble in an aqueous solution. Further, creatine is not well absorbed from the gastrointestinal (GI) tract, which has been estimated to have a 1 to 14 percent absorption rate. Thus, current products require large amounts of creatine to be administered to be effective, typically 5 grams or more. Additionally, side effects such as bloating, gastrointestinal (GI) distress, diarrhea, and the like are encountered with these high dosages.

Therefore, it would be desirable to provide an improved approach for enhancing absorption of creatine.

SUMMARY OF THE INVENTION

Accordingly, the present invention is directed to creatine ester pronutrients and formulations. In a first aspect of the present invention, a method for providing creatine to an animal includes receiving a creatine ester by the animal. The creatine ester is suitable for being modified by the animal to form creatine. In a second aspect of the present invention, a food supplement includes a creatine ester suitable for being modified by an animal to form creatine. In a third aspect of the present invention, a method for providing creatine to an animal includes receiving an ester derivative of creatine by the animal. The ester derivative of creatine is suitable for acting as a pronutrient in an animal.

In a fourth aspect of the present invention, a composition of matter includes:

wherein R represents an ester.

In a fifth aspect of the present invention, a method of producing a creatine pronutrient includes reacting a hydrated form of creatine with an alcohol in an acidic environment wherein a product is formed including a creatine ester pronutrient.

It is to be understood that both the forgoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Reference will now be made in detail to the presently preferred embodiments of the invention, examples of which are illustrated in the accompanying drawings.

Referring generally now to FIGS. 1 through 5, exemplary embodiments of the present invention are shown. Creatine, N-aminoiminomethyl-N-methylglycine, is an endogenous nutrient which may be produced in the liver and kidneys. Typically, creatine is produced by the transfer of the guanidine moiety of arginine to glycine, which is then methylated to give creatine. Creatine may be represented by the following formula:

Creatine phosphate is formed in the body and may be represented by the following formula:

Creatine is converted to creatine phosphate by the creatine kinase enzyme. The creatine phosphate transfers its phosphate to adenosine diphosphate (ADP) to accomplish the regeneration of adenosine triphosphate (ATP). Adenosine triphosphate (ATP) may then be utilized by the muscles as a source of energy. Thus, by providing a formulation and method for enhanced absorption of creatine, the muscle levels of phosphocreatine will be elevated. As a result of this, muscle mass and performance may be increased, thereby permitting a variety of therapeutic applications.

Studies in the laboratory have shown that the aqueous solubility and partition coefficient of creatine monohydrate are 15.6±2.1 mg/mL and 0.015±0.007, respectively. The low oral bioavailability of creatine may derive not only from its low lipophilicity and concomitant poor membrane permeability, but also from rapid conversion to creatinine in the acidic condition of the stomach, and shown in FIG. 1A.

Figure 1A:
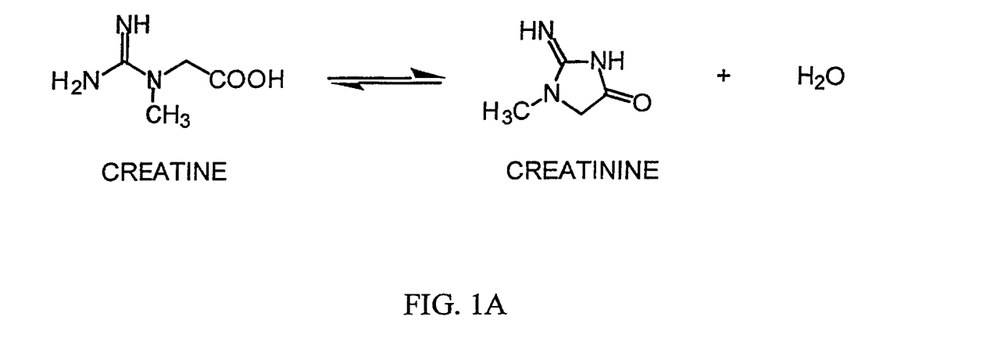
FIG. 1A is an illustration depicting conversion of creatine to creatinine.

At a gastric pH range of 1-2, the equilibrium between creatine and creatinine shifts to the right such that the creatinine/creatine ratio may be greater than or equal to 30. See Edgar, G.; Shiver, H. E., *The Equilibrium Between Creatine and Creatinine in Aqueous Solution. The Effect of Hydrogen Ion.* J. Amer. Chem. Soc. 1925, 47, 1179-1188, which is herein incorporated by reference in its entirety.

Figure 1B:
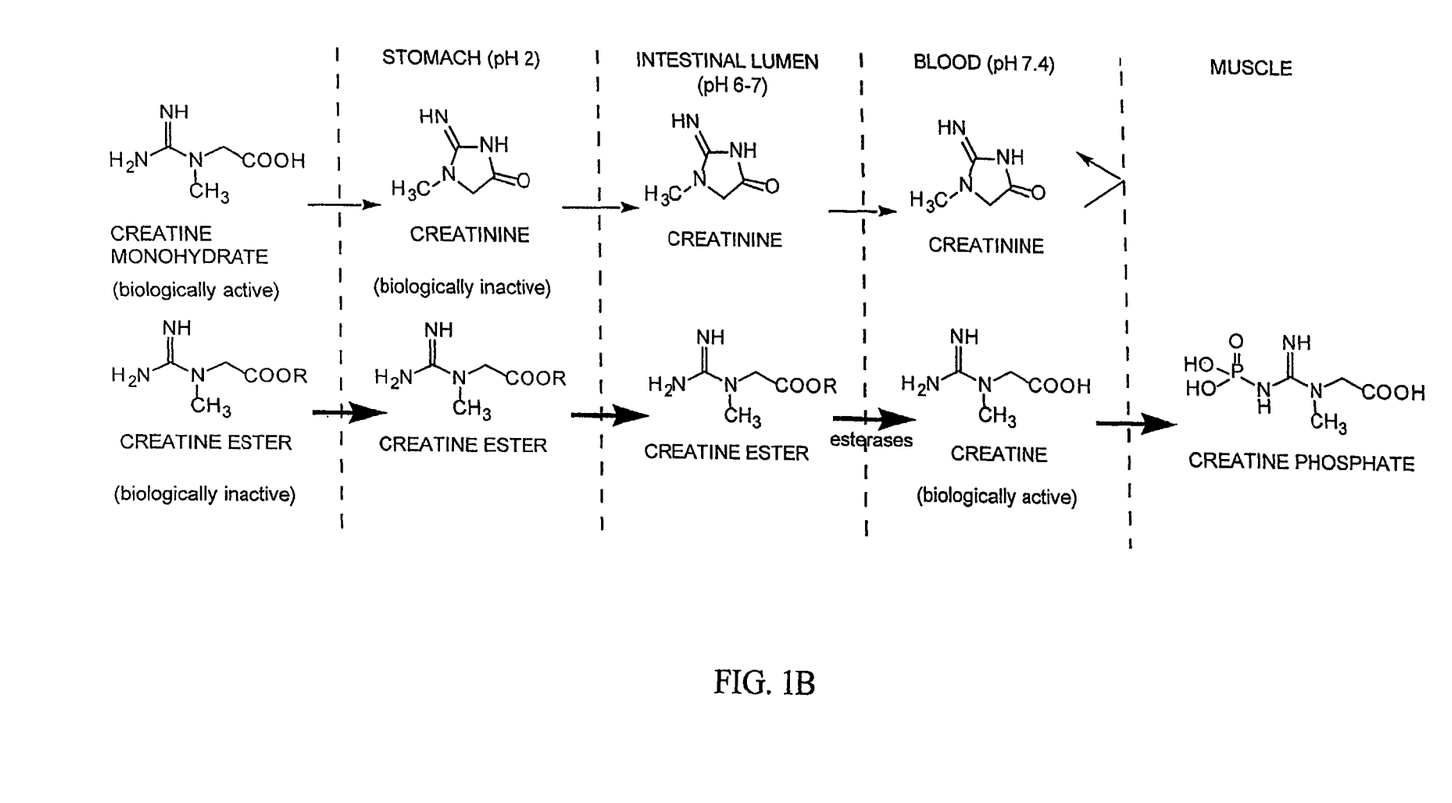
FIG. 1B is a depiction of an exemplary embodiment of the present invention wherein the processing of creatine monohydrate versus a creatine ester by the body is shown.

Referring now to FIG. 1B, an embodiment of the present invention is shown wherein creatine ester metabolism is shown. By providing a creatine ester, a more water-soluble compound will be provided than the relatively insoluble zwitterionic creatine, and increased lipophilicities will allow for better membrane permeability.

For example, by masking the carboxylic acid functional group of creatinine by esterification, the formation of creatinine in the stomach will be precluded, resulting in an efficient delivery of the creatine esters to the intestine where absorption may occur. Standard supplements containing creatine monohydrate undergo substantial conversion to creatinine in the stomach. This, coupled with the low absorption of creatine in the intestine, leads to reduced amounts of creatine reaching the muscle cell.

In contrast, creatine esters do not undergo conversion to creatinine in the stomach and are more readily absorbed in the intestine. As a result, blood creatine concentrations are higher and thus more creatine is available to the muscle. As a result of this, the intestinal absorption of creatine ester will be significantly greater than that observed with creatine monohydrate. An additional advantage of creatine esters is that, as the creatine ester compound moves from the intestinal tissue into the bloodstream, the creatine ester compounds themselves are biologically inactive, but esterase enzymes present in both the intestinal cells and the blood break the ester bonds of creatine ester, converting it to biologically active creatine. In other words, the advantages of the creatine ester are preserved during transport, such as increased solubility and permeability, but when needed, the creatine is available to be converted into its biologically active form.

Compared to creatine monohydrate, the increased blood levels of creatine obtained with supplements containing the creatine ester compounds are expected to result in increased responses at the target tissue (i.e. muscle). Thus the increased stability and improved absorption of creatine ester results in much greater blood creatine levels than can be achieved with creatine monohydrate supplements. Once in the blood, creatine is transported into the muscle cells, where it is converted to creatine phosphate that will then be consumed by the cell during muscle performance.

Following is a brief overview of the various disease states that may be responsive to creatine supplementation. It should be noted that the proposed disease states below involve increasing creatine in a diverse array of cells including not only muscle but neurons and endothelial cells as well.

Parkinson's Disease

Parkinson's disease depletes dopamine levels in the brain. Energy impairment may play a role in the loss of dopaminergic neurons. Studies involving rats showed that a diet supplemented with creatine for 2 weeks resulted in only a 10% reduction in brain dopamine as compared to a 70% dopamine depletion in nonsupplemented rodents. See Matthews R T, Ferrante R J, Klivenyi P, Yang L, Klein A M, Mueller G, Kaddurah-Daouk R and Beal M F. *Creatine and cyclocreatine attenuate MPTP neurotoxicity.* Exp Neurol 157: 142-149, (1999), which is herein incorporated by reference in its entirety. These pre-clinical studies suggest that creatine dietary supplements may have a positive therapeutic outcome in slowing the onset and decreasing the severity of the disease.

Huntington's Disease

Alterations in energy production may also contribute to the development of brain lesions in patients with Huntington's disease. Rats fed a diet supplemented with creatine for 2 weeks responded better when exposed to 3-nitropropionic acid which mimics the changes in energy metabolism seen with Huntington's disease. The creatine fed animals had 83% less lesion volume than nonsupplemented animals (Matthews et al., 1999).

Mitochondrial Pathologies

Creatine supplementation increased the life-span of GP3A transgenic mice (a model for amyotrophic lateral sclerosis) up to 26 days. A study involving patients with a variety of neuromuscular disorders also benefited from creatine supplementation. See Klivenyi P, Ferrante R J, Matthews R T, Bogdanov M B, Klein A M, Andreassen O A, Mueller G, Wermer M, Kaddurah-Daouk R and Beal M F. *Neuroprotective effects of creatine in a transgenic animal model of amyotrophic lateral sclerosis*. Nat Med 5: 347-350, (1999), which is herein incorporated by reference in its entirety. Increases in high-density strength measurements were seen in these patients following a short-term trail of creatine (10 g/d for 5 days with 5 g/d for 5 to 7 days). Creatine supplementation also resulted in increased body weight in these patients.

Stroke

Creatine may also be useful in patients with hypoxia and ishemic brain diseases such as stroke. Creatine has been shown to reduce damage to the brainstem and hippocampus resulting from hypoxia. See Balestrino M, Rebaudo R and Lunardi G. *Exogenous creatine delays anoxic depolarization and protects from hypoxic damage: Dose-effect relationship*. Brain Res 816:124-130, (1999); and Dechent P, Pouwels P J, Wilken B, Hanefeld F and Frahm J. *Increase of total creatine in human brain after oral supplementation of creatine-monohydrate*. Am J Physiol 277: R698-R704, (1999) which are herein incorporated by reference in their entirety. This neuroprotection may be due to prevention of ATP depletion. Studies suggest that supplementation of humans with creatine does increase brain levels of creatine. See Wick M, Fujimori H, Michaelis T and Frahm J. *Brain water diffusion in normal and creatine-supplemented rats during transient global ischemia*. Magn Reson Med 42: 798-802, (1999); Michaelis T, Wick M, Fujimori H, Matsumura A and Frahm J. *Proton MRS of oral creatine supplementation in rats. Cerebral metabolite concentrations and ischemic challenge*. NMR Biomed 12: 309-314, (1999); and Malcon C, Kaddurah-Daouk R and Beal M. *Neuroprotective effects of creatine administration against NMDA and malonate toxicity*. Brain Res 860: 195-198, (2000) which are herein incorporated by reference in their entirety. High brain creatine levels may offer protection to ischemic brain injury.

Muscular Diseases

Patients with various muscular dystrophies supplemented with creatine for 8 weeks showed a 3% increase in strength and a 10% improvement in neuromuscular symptom score. Short-term creatine supplementation also improved strength in patients with rheumatoid arthritis, but did not change physical function. See Felber S, Skladal D, Wyss M, Kremser C, Koller A and Sperl W. *Oral creatine supplementation in Duchenne muscular dystrophy: A clinical and 31P magnetic resonance spectroscopy study*. Neurol Res 22: 145-150 (2000), which is herein incorporated by reference in its entirey. Patients with McArdles disease showed improvements when given creatine. The improvements included reduced frequency of muscle pain and increased exercise performance and strength. Increases in exercise performance were also seen during ischemic episodes. See Willer B, Stucki G, Hoppeler H, Bruhlmann P and Krahenbuhl S. *Effects of creatine supplementation on muscle weakness in patients with rheumatoid arthritis*. Rheumatology 39: 293-298, (2000), which is herein incorporated by reference in its entirety.

Heart Disease

Given the role of creatine phosphate as an immediate and readily accessible source of phosphate for regeneration of ATP, it follows that creatine supplementation may have a favorable impact diseases of the heart. In patients with congestive heart failure creatine supplementation produced an increase in exercise performance as measured by strength and endurance. See Gordon A, Hultman E, Kaijser L, Kristjansson S, Rolf C J, Nyquist O and Sylven C. *Creatine supplementation in chronic heart failure increases skeletal muscle creatine phosphat and muscle performanmce*. Cardiovasc Res 30: 413-418, (1995), which is herein incorporated by reference in its entirety. An additional consideration with ramifications in the management of cardiovascular diseases is the report that creatine supplementation can lower cholesterol and triglyceride levels in humans. See Earnest C P, Almada A L and Mitchell T L. *High-performance capillary electrophoresis pure creatine monohydrate reduces blood lipids in men and women*. Clin Sci (Colch) 91: 113-118, (1996), which is herein incorporated by reference in its entirety.

Muscle Fatigue Secondary to Aging

Research on adults over 60-years of age suggest that creatine supplementation may delay muscle fatigue, but does not affect body composition or strength (Rawson and Clarkson, 2000). See Rawson E S and Clarkson P M. *Acute creatine supplementation in older men*. Int J Sports Med 21: 71-75, (2000), which is herein incorporated by reference in its entirety. As with many of the therapeutic implication studies, these preliminary experiments were performed over a short (i.e. less than 30-day) period of time, where the effects of creatine supplementation on muscle mass and strength may not be fully demonstrated. While the effects observed in the elderly were not profound, these initial reports suggest the health benefits to this growing population are promising.

Figure 1C:
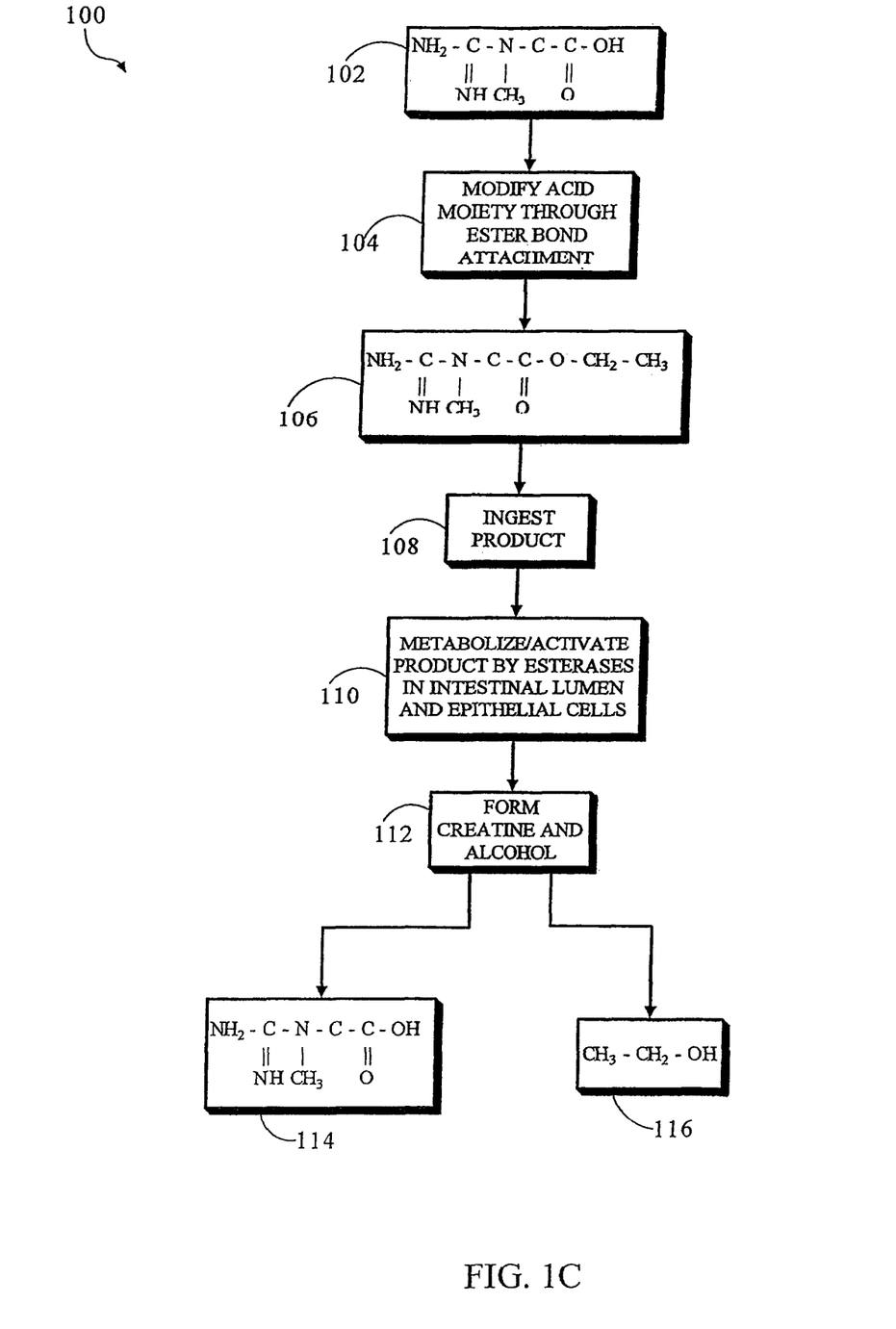
FIG. 1C is a flow diagram illustrating an exemplary embodiment of the present invention wherein a pronutrient derivative of creatine is created through the modification of an acid moiety by ester bond attachment.

Referring now to FIG. 1C, an exemplary embodiment of the present invention is shown wherein a pronutrient derivative of creatine is created through the modification of an acid moiety by ester bond attachment. Creatine 102 is changed by modifying an acid moiety through ester bond attachment 104. For example, creatine may be converted to creatine ethyl ester 106, which has a formula as follows:

A creatine ester has the advantages of increased aqueous solubility, increased absorption from the gastrointestinal (GI) tract resulting in increased bioavailability, and increased stability, especially for solution formulations. Increased bioavailability allows smaller doses to be utilized with greater effect, thereby resulting in fewer gastrointestinal side effects. Further, more varied formulation possibilities are feasible, for example, the product may be formulated in tablet or capsule form with dextrose and/or phosphate for ease of use and effectiveness.

Once the product is ingested 108, the body metabolizes and activates the product by esterases 110, which may be found in the intestinal lumen, epithelial cells and the blood. The esterases convert the product to creatine 114 and an alcohol 116. Thus, the current invention supplements the amount of creatine normally available to the muscle thereby increasing phosphocreatine levels and decreasing the recovery time required before the muscle can perform activity.

Further, the resultant alcohols, such as ethanol, glycerol, benzyl alcohol, tert-butyl alcohol, are relatively harmless. See Budavari, S. (Ed.) The Merck Index. Merck and Co., Inc., Whitehouse Station, N.J., 1996, which is herein incorporated by reference in its entirety. For example, benzyl alcohol is used as a pharmaceutical preservative.

Figure 1D:
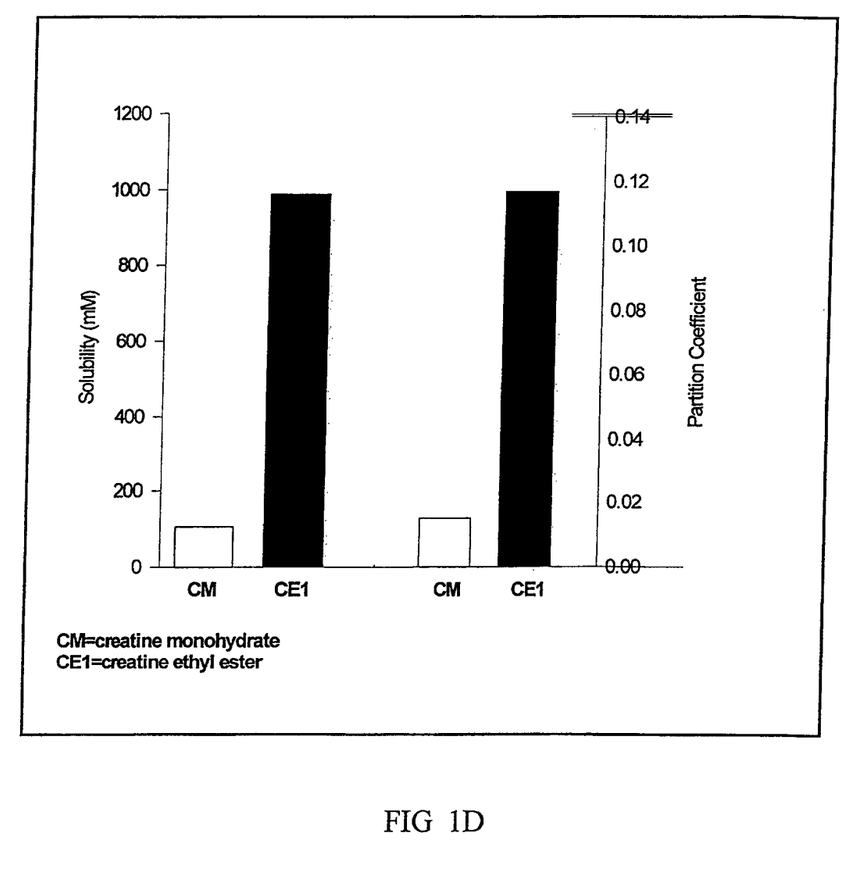
FIG. 1D is an illustration of an embodiment of the present invention in which a graph depicting solubility and partition coefficients of creatine ethyl ester versus creatine monohydrate are shown.
Figure 2A:
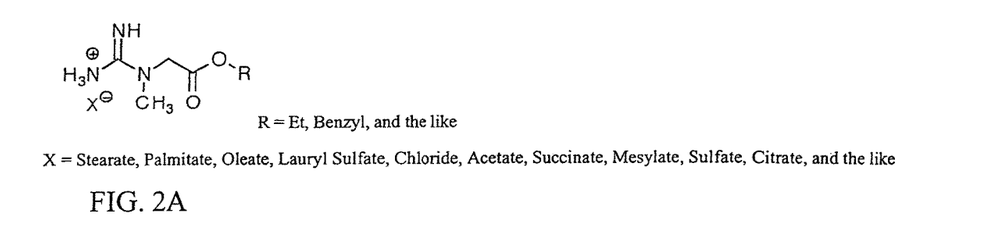
FIGS. 2A, 2B, 2C, 2D, 2E, 2F, 2G, 2H, 2I, 2J, 2K, 2L, 2M and 2N are illustrations of exemplary compounds of the present invention.
Figure 2B:
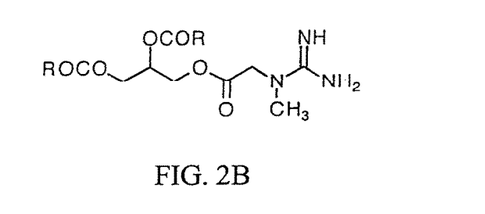
Figure 2C:
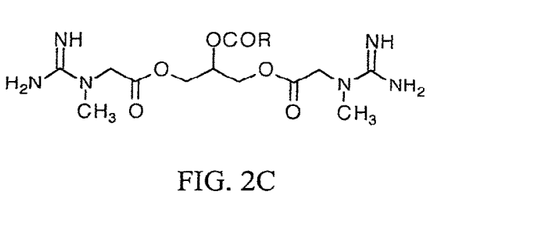
Figure 2D:
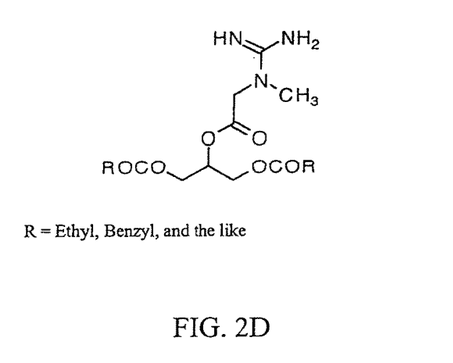
Figure 2E:
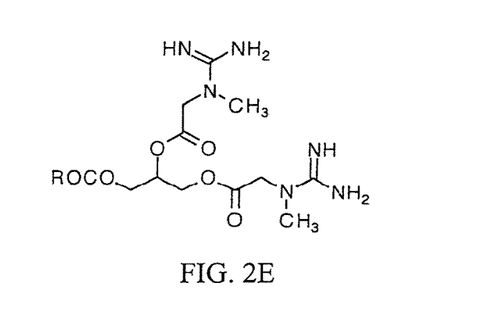
Figure 2F:
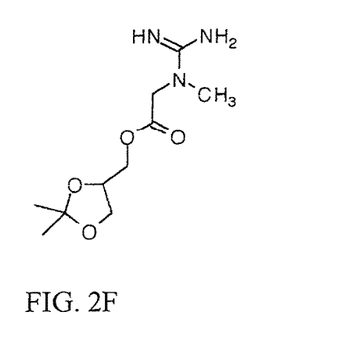
Figure 2G:
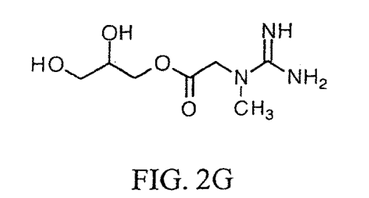
Figure 2H:
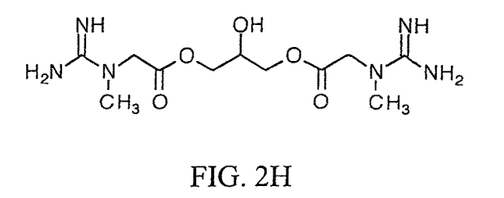
Figure 2I:
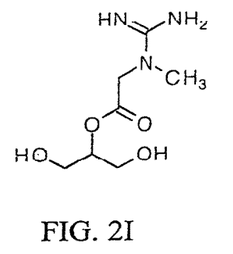
Figure 2J:
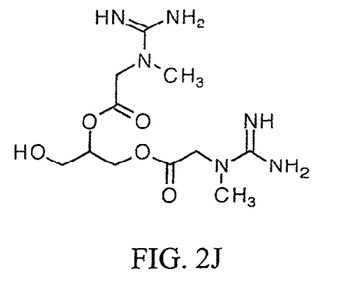
Figure 2K:
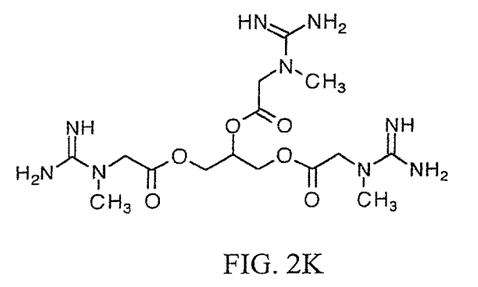
Figure 2L:
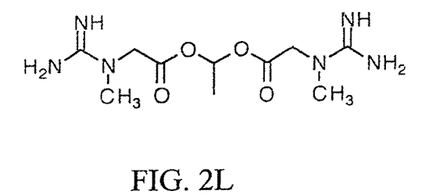
Figure 2M:
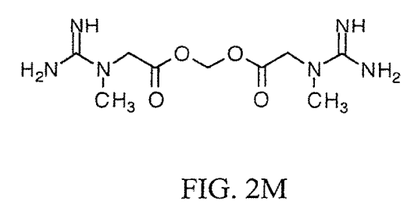
Figure 2N:
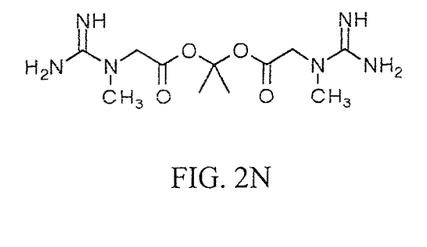

Solubility and permeability are two important factors in the amount of a compound made available to an organism, otherwise known as bioavailability. Solubility refers to the amount of the compound that may be dissolved, wherein permeability refers to the ability of the compound to penetrate across a barrier, such as a membrane, cell wall and the like. In terms of solubility, creatine ethyl ester is a great deal more soluble that creatine. Utilizing a physiological buffer solution (PBS), laboratory analysis indicates that creatine monohydrate has a solubility limit of approximately 10 mg/ml. This value may be overly generous, as a great deal of vortexing of the sample and brief heating of the sample to 37 degrees Celsius had to be performed to even achieve that result. However, the creatine ethyl ester is readily soluble in room temperature PBS with solubility over 200 mg/ml.

With regard to permeability, a laboratory analysis was performed comparing the creatine monohydrate to creatine ethyl ester in MDCK monolayers. The MDCK are a canine kidney epithelial cell line that has been used as an in vitro model for assessing drug permeability. In the MDCK monolayers, creatine monohydrate showed approximately 10% flux over one hour. In other words, 10% of the original amount of creatine monohydrate added to one side of the MDCK monolayer made it across to the other side in a 60-minute period. For creatine ethyl ester, the permeability is quite higher, averaging approximately 20% flux over one hour. Similar results are expected in a Caco-2 monolayer, which may be used as an in vitro model for intestinal absorption. Thus, the creatine ester of the present invention has the unexpected result of both increased solubility and membrane permeability, and thus greater bioavailability, as shown through the following table and graph depicted in FIG. 1D.

| Substance | Conc. at Saturation mg/ml | Partition Coefficient |
| --- | --- | --- |
| Creatine | 15.6 +/− 2.1 | 0.015 +/− 0.007 |
| Creatine Ethyl Ester | 205.9 +/− 1.5 | 0.074 +/− 0.008 |
| Creatine Benzyl Ester | 89.26 +/− 0.8 | 0.106 +/− 0.01 |

Although a creatine ethyl ester compound has been described, it should be apparent that a wide variety of creatine ester compounds and salts thereof are contemplated by the present invention without departing from the spirit and scope thereof, examples of which are shown in FIGS. 2A, 2B, 2C, 2D, 2E, 2F, 2G, 2H, 2I, 2J, 2K, 2L, 2M and 2N. For example, a mono-creatine glycerol, di-creatine glycerol, tricreatine glycerol and the like, may be utilized as a pronutrient of the present invention, the formula for a tricreatine glycerol is as follows:

Another example of a creatine ester compound suitable for use as a pronutrient includes creatine phosphoester, the formula of which is as follows:

Thus, the present invention provides multiple ester derivatives of creatine for use as pronutrients having increased solubility and permeability over creatine itself. The advantages of creatine pronutrients of the present invention would be useful in athletic performance markets, therapeutic markets targeting patients with diseases involving reduced muscle performance/loss of muscle mass, livestock/animal food products market, and the like.

Figure 3:
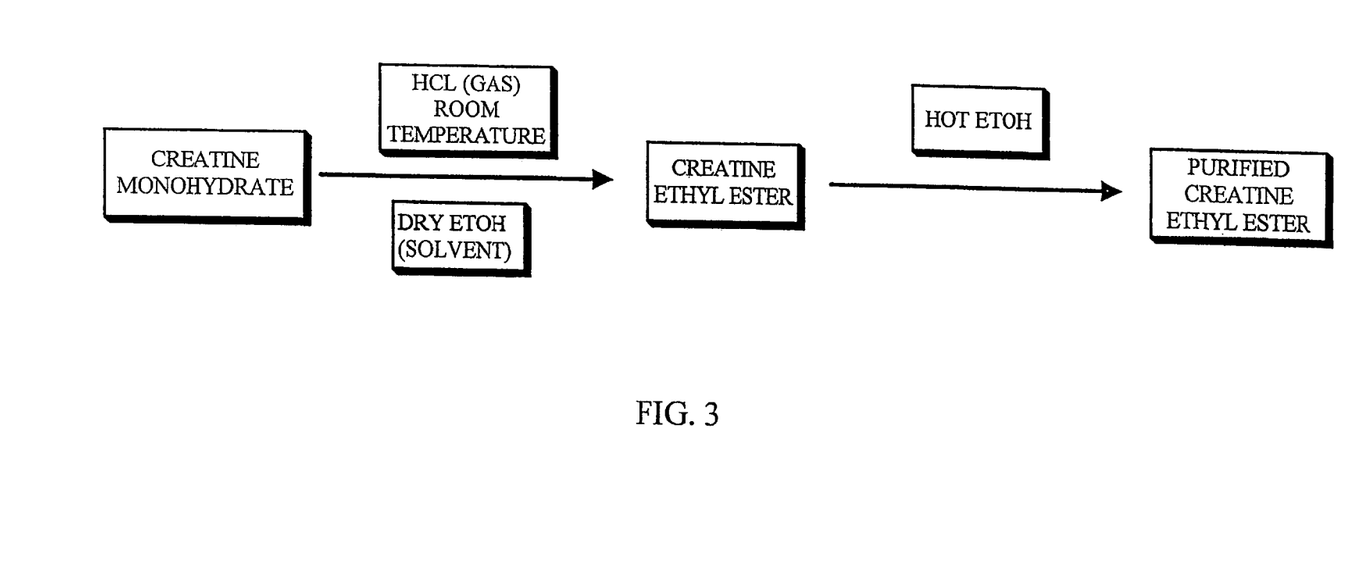
FIG. 3 is an illustration depicting an exemplary embodiment of the present invention wherein a creatine ethyl ester compound is produced by solvating creatine monohydrate in dry ethyl alcohol in an acidic atmosphere.
Figure 4:
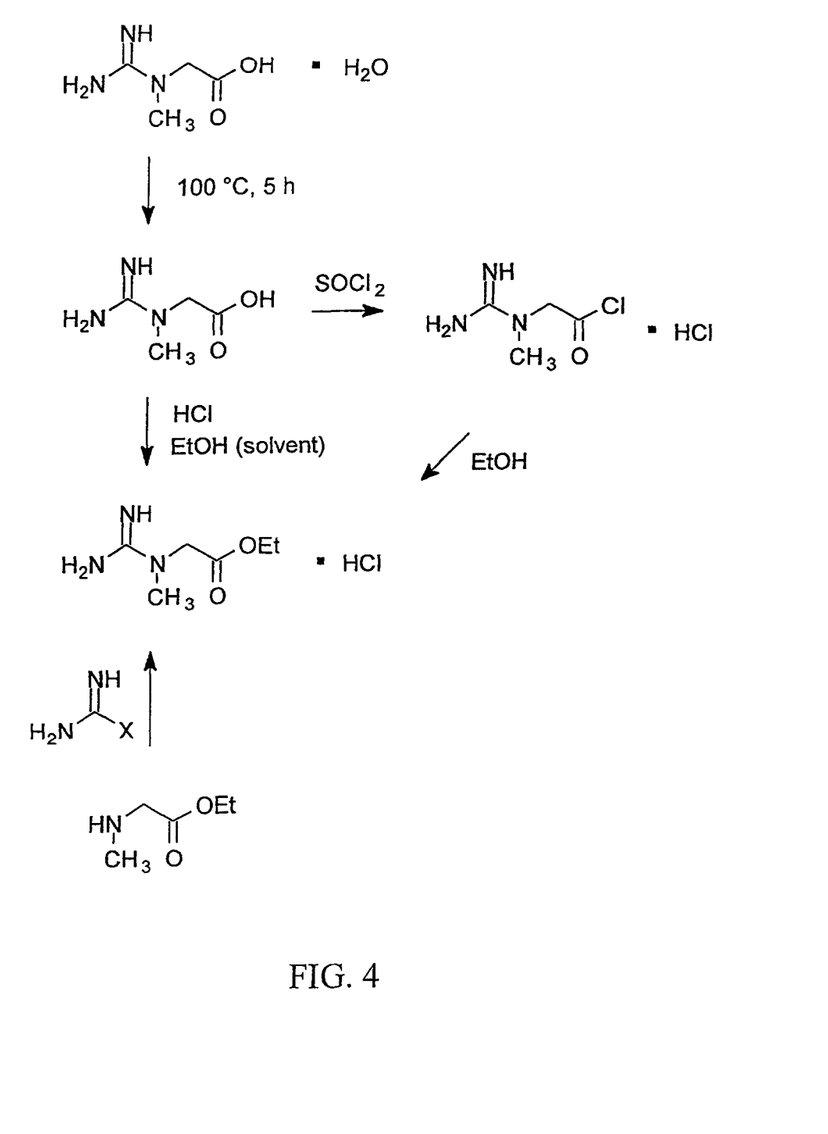
FIG. 4 is an illustration of an embodiment of the present invention wherein additional methods and processes are shown for the production of a creatine ester.

Referring generally now to FIGS. 3 and 4, an exemplary embodiment of the present invention is shown wherein the production of an ester derivative of creatine is shown. A creatine ester may be formed by reacting a hydrated form of creatine or anhydrous creatine with various alcohols in an acidic atmosphere. Under these conditions, various ester procreatine compounds may be formed, generally as white precipitates. The resultant creatine esters may be further purified by solvating in an alcohol at elevated temperatures and then cooling to form the ester procreatine compound. The final recrystallization step may not be required, as the initial precipitate is generally pure. However, such an extra step may be useful to ensure that the purest form of the creatine pronutrient has been obtained.

For example, as shown in FIG. 3, creatine monohydrate may be solvated in dry ethyl alcohol in an atmosphere of hydrochloric acid at ambient temperatures. The resultant creatine ethyl ester compound is solid at ambient temperatures. While not functionally necessary, the resultant creatine ethyl ester may be further purified with the use of ethyl alcohol at an elevated temperature to solvate the creatine ethyl ester away from possible contaminates contained in the solid reaction material. Purified creatine ethyl ester may then be achieved upon cooling the solvated creatine ethyl ester. It should also be apparent that anhydrous creatine may also be utilized without departing from the spirit and scope of the present invention.

Although the formulation of creatine ethyl ester is disclosed, it should be apparent that a variety of creatine esters may be produced utilizing analogous reaction systems without departing from the spirit and scope of the present invention. See Dox., A. W.; Yoder, L. Esterification of Creatine. J. Biol. Chem. 1922, 67, 671-673, which is herein incorporated by reference in its entirety. For instance, a variety of methods of producing a creatine ester are contemplated without departing from the spirit and scope of the present invention, such as the methods and process shown in FIG. 4, wherein X may include a leaving group. Although the use of creatine monohydrate is disclosed, a variety of creatine containing starting compounds are contemplated by the present invention, creatine monohydrate being disclosed merely because of its availability.

Figure 5:
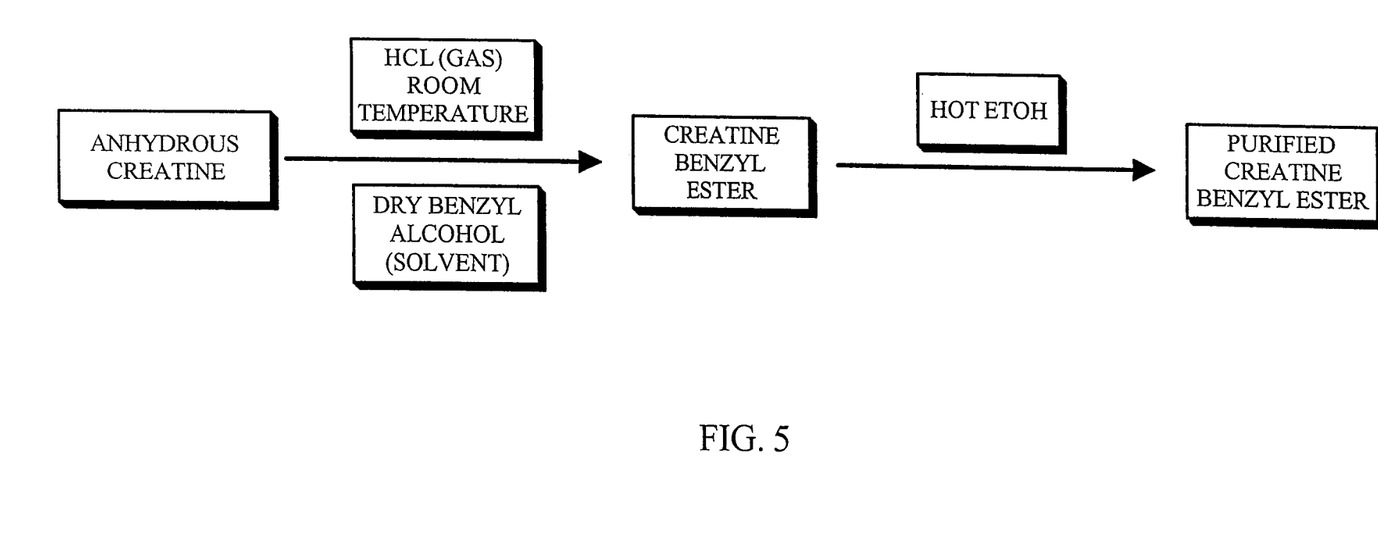
FIG. 5 is an illustration depicting an exemplary embodiment of the present invention wherein a creatine benzyl ester compound is produced by solvating anhydrous creatine in dry benzyl alcohol in an acidic atmosphere.

Referring now to FIG. 5, an embodiment of the present invention is shown wherein anhydrous creatine is solvated in dry benzyl alcohol in an atmosphere of hydrochloric acid at ambient temperatures to produce a creatine ester. The resultant creatine benzyl ester compound is a white solid at ambient temperatures. While not functionally necessary, the resultant creatine benzyl ester may be further purified with the use of ethyl alcohol at an elevated temperature to solvate the creatine benzyl ester away from possible contaminates. Purified creatine benzyl ester may then be achieved upon cooling the solvated creatine benzyl ester. As stated earlier, the final recrystallization step may not be required as the initial precipitate is relatively pure. However, such an extra purification step may be useful to ensure that the most pure form of the compound has been obtained.

As discussed earlier, creatine esters may also be synthesized from anhydrous creatine using esterification methods and isolated as their hydrochloride salts. For example, creatine ethyl ester hydrochloride may be synthesized by treatment of anhydrous creatine with ethanolic HCl at room temperature. See Dox., A. W.; Yoder, L. *Esterification of Creatine*. J. Biol. Chem., 67, 671-673, (1922) which is herein incorporated by reference in its entirety.

creatine ethyl ester hydrochloride

Using this method, creatine ethyl ester hydrochloride was synthesized in 74% yield after a single recrystallization from ethanol.

creatine benzyl ester hydrochloride creatine monoglycerate ester hydrochloride

Creatine esters creatine benzyl ester hydrochloride and creatine monoglycerate ester hydrochloride may similarly be obtained by exposure of anhydrous creatine with excess HCl-saturated benzyl alcohol and glycerol, respectively. It should be apparent that stereoisomers, such as a stereoisomers of creatine monoglycerate ester hydrochloride, and the compounds shown in FIGS. 2B, 2E, 2F, 2G, 2J and the like, are also contemplated by the present invention.

creatine tert-butyl ester hydrochloride

Creatine tert-butyl ester hydrochloride may be obtained by treatment of creatine acid chloride with tert-butanol and zinc chloride. See Rak, J.; Lubkowski, J.; Nikel, I.; Przubulski, J.; Blazejowski, J. *Thermal Properties, Crystal Lattice Energy, Mechanism and Energetics of the Thermal Decomposition of Hydrochlorides of 2-Amino Acid Esters*, Thermochimica Acta 171, 253-277 (1990); Yadav, J. S.; Reddy, G. S.; Srinivas, D.; Himabindu, K. *Zinc Promoted Mild and Efficient Method for the Esterification of Acid Chlorides with Alcohols*, Synthetic Comm. 28, 2337-2342 (1998). Creatine tert-butyl ester hydrochloride may also be obtained by treatment of anhydrous creatine with tert-butanol and anhydrous magnesium sulfate and catalytic sulfuric acid. See Wright, S. W.; Hageman, D. L.; Wright, A. S.; McClure, L. D. *Convenient Preparations of t-Butyl Esters and Ethers from t-Butanol*, Tetrahedron Lett. 38, 7345-7348 (1997), which are herein incorporated by reference in their entireties.

bis creatine glycerate ester dihydrochloride

Bis creatine glycerate ester dihydrochloride ester, may be obtained by treatment of creatine acid chloride with a half-molar equivalent of anhydrous glycerol. See Rak, J.; Lubkowski, J.; Nikel, I.; Przubulski, J.; Blazejowski, J. *Thermal Properties, Crystal Lattice Energy, Mechanism and Energetics of the Thermal Decomposition of Hydrochlorides of 2-Amino Acid Ester*, Thermochimica Acta 71, 253-277 (1990), which is herein incorporated by reference in its entirety.

Alternatives to these methods include transesterification reaction of CE1 using either catalytic diphenyl ammonium triflate and trimethylsilyl chloride (Wakasugi et al., 2000) or catalytic potassium tert-butoxide and 1 equivalent of tert-butyl acetate. Creatine acid chloride may also be used rather than anhydrous creatine in the esterification reactions. See Wakasugi, K.; Misake, T.; Yamada, K.; Tanabe, Y. *Diphenylammonium triflate (DPAT): Efficient Catalyst for Esterification of Carboxylic Acids and For Transesterification of Carboxylic Esters With Nearly Equimolar Amounts of Alcohols*, Tetrahedron Lett. 41, 5249-5252 (2000), which is herein incorporated by reference in its entirety.

Regioselectivity problems in the formation of creatine esters, such as creatine monoglycerate ester hydrochloride, Bis creatine glycerate ester dihydrochloride ester, and the like, may be addressed by selective esterification of the primary alcohol functional group(s) of glycerol with creatine acid chloride in the presence of N,N-diisopropylethylamine or 2,4,6-collidine at low temperatures. See Ishihara, K.; Kurihara, H.; Yamamoto, H. *An Extremely Simple, Convenient, and Selective Method for Acetylating Primary Alcohols in the Presence of Secondary Alcohols*, J. Org Chem. 58, 3791-3793 (1993), which is herein incorporated by reference in its entirety.

Creatine esters may be purified by crystallization, flash column chromatography, and the like, if desired, and the structures and purity confirmed by analytical HPLC, $^1$H and $^{13}$C NMR, IR, melting point and elemental analysis. The following data was obtained through nuclear magnetic resonance spectroscopy of the corresponding compounds:

Creatine ethyl ester hydrochloride $^1$H NMR (500 MHz, CDCl$_3$) δ 1.12 (dq, J=6.0 Hz, J=1.0 Hz, 3H), 2.91, (s, 3H), 4.10-4.11 (m, 4H).

Creatine benzyl ester hydrochloride $^1$H NMR (500 MHz, DMSO-$d_6$) δ 3.03 (s, 3H), 4.13 (s, 2H). 5.06 (s, 2H), 7.22-7.38 (m, 5H).

It is understood that the specific order or hierarchy of steps in the methods disclosed are examples of exemplary approaches. Based upon design preferences, it is understood that the specific order or hierarchy of steps in the method can be rearranged while remaining within the scope of the present invention. The accompanying method claims present elements of the various steps in a sample order, and are not meant to be limited to the specific order or hierarchy presented.

It is believed that the creatine ester pronutrient compounds and formulations of the present invention and many of its attendant advantages will be understood by the forgoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof. It is the intention of the following claims to encompass and include such changes.

What is claimed is:

1. An oral supplement consisting of creatine ethyl ester hydrochloride suitable for being modified by an animal to form creatine.

2. The oral supplement according to claim 1, wherein the creatine ethyl ester hydrochloride is suitable for being formulated in a solid form capable of being ingested by the animal.

3. The oral supplement according to claim 2, wherein the solid form is configured as at least one of a tablet and a capsule.

4. The oral supplement according to claim 1, wherein the creatine ethyl ester hydrochloride is formulated for liquid delivery.

5. The oral supplement according to claim 4, wherein the creatine ethyl ester hydrochloride is formulated as an aqueous solution or emulsion.

6. The oral supplement according to claim 1, wherein the creatine ethyl ester hydrochloride is received by the animal, the creatine ethyl ester hydrochloride is modified by the animal into creatine and an alcohol.

7. The oral supplement according to claim 6, wherein the creatine ethyl ester hydrochloride is modified by the animal into creatine and alcohol by an esterase.

8. The oral supplement according to claim 6, wherein the creatine ethyl ester hydrochloride is modified by at least one of an intestinal lumen, epithelial cell and blood of the animal into creatine.

9. An oral supplement for ingestion by an animal, consisting of creatine ethyl ester hydrochloride, wherein the creatine ethyl ester hydrochloride exhibits a solubility in room temperature physiological buffer solution that is at least about 20 times greater than that of creatine monohydrate.

10. The oral supplement of claim 9, wherein the food supplement is in solid form.

11. The oral supplement of claim 10, wherein the solid form is configured as at least one of a tablet and a capsule.

12. The oral supplement of claim 9, wherein the food supplement is in liquid form.

13. The oral supplement of claim 12, wherein the liquid form is an aqueous solution or emulsion.

14. An oral supplement for ingestion by an animal consisting of creatine ethyl ester hydrochloride suitable for being modified by an animal to form creatine, wherein the creatine ethyl ester hydrochloride possesses a solubility of at least 200 mg/ml in room temperature physiological buffer solution.

15. The oral supplement of claim 14, wherein the food supplement is in solid form.

16. The oral supplement of claim 15, wherein the solid form is configured as at least one of a tablet and a capsule.

17. The oral supplement of claim 14, wherein the food supplement is in liquid form.

18. The oral supplement of claim 17, wherein the liquid form is an aqueous solution or emulsion.

* * * * *